United States Patent [19]
Ackerson

[11] Patent Number: 6,100,976
[45] Date of Patent: Aug. 8, 2000

[54] METHOD AND APPARATUS FOR FIBER OPTIC MULTIPLE SCATTERING SUPPRESSION

[75] Inventor: Bruce J. Ackerson, Stillwater, Okla.

[73] Assignee: The Board of Regents for Oklahoma State University, Stillwater, Okla.

[21] Appl. No.: 09/157,733

[22] Filed: Sep. 21, 1998

Related U.S. Application Data

[60] Provisional application No. 60/059,619, Sep. 23, 1997.

[51] Int. Cl.[7] .................................................. G01N 15/02
[52] U.S. Cl. ........................... 356/336; 356/338; 356/343
[58] Field of Search .................................... 356/335, 336, 356/338, 322, 341; G01N 15/02

[56] References Cited

U.S. PATENT DOCUMENTS

| | | | |
|---|---|---|---|
| 4,676,641 | 6/1987 | Bott | 356/336 |
| 4,854,705 | 8/1989 | Bachalo | 356/336 |
| 5,090,808 | 2/1992 | Ishikawa et al. | 356/336 |
| 5,155,549 | 10/1992 | Dhadwal . | |
| 5,396,333 | 3/1995 | Aleshin et al. . | |
| 5,502,561 | 3/1996 | Hutchins et al. . | |
| 5,513,004 | 4/1996 | Naqwi et al. . | |
| 5,621,523 | 4/1997 | Oobayashi et al. . | |

OTHER PUBLICATIONS

Nobbmann et al, Multiple–scattering suppression: cross correlation with tilted single mode fibers, Applied Optics, vol.36, No. 30, Oct. 1997.

Ackerson, B.J., R.L. Dougherty, N.M. Reguigui, and U. Nobbmann: "Correlation Transfer: Application of Radiative Transfer Solution Methods to Photon Correlation Problems", *Journal of Thermophysics and Heat Transfer*, vol. 6, No. 4, Oct.–Dec. 1992, pp. 577–588.

Brown, R.G.W.: "Dynamic light scattering using monomode optical fibers", *Applied Optics*, vol. 26, Nov. 15, 1987, pp. 4846–4851.

Dhont, J.K.G. and C.G. de Kruif: "Scattered light intensity cross correlation. I. Theory", *J. Chem. Phys.*, vol. 79, No. 4, Aug. 15, 1983, pp. 1658–1663.

Durian, D.J., D.A. Weitz, and D.J. Pine; "Multiple Light–Scattering Probes of Foam Structure and Dynamics", *Science*, vol. 252, May 1991, pp. 686–688.

Lock, James A.: "Role of multiple scattering in cross–correlated light scattering with a single laser beam", *Applied Optics*, vol. 36, No. 30, Oct. 20, 1997, pp. 7559–7570.

Mandel, L. and E. Wolf. *Optical coherence and quantum optics*. Cambridge University Press, pp.188–193, 428–429.

Meyer, W.V., D.S. Cannell, A.E. Smart, T.W. Taylor and P. Tin: "Multiple–scattering suppression by cross correlation", *Applied Optics*, vol. 36, No. 30, Oct. 20, 1997, pp. 7551–7570.

Phillies, G.D.J.: "Suppression of multiple scattering effects in quasielastic light scattering by homodyne cross–correlation techniques", *J. Chem. Phys.*, vol. 74, No. 1, Jan. 1, 1981, pp. 260–262.

(List continued on next page.)

*Primary Examiner*—Robert H. Kim
*Assistant Examiner*—Layla Lauchman
*Attorney, Agent, or Firm*—Fellers, Snider, Blankenship, Bailey & Tippens, P.C.

[57] ABSTRACT

The instant invention provides a method and apparatus for use in laser induced dynamic light scattering which attenuates the multiple scattering component in favor of the single scattering component. The preferred apparatus utilizes two light detectors that are spatially and/or angularly separated and which simultaneously record the speckle pattern from a single sample. The recorded patterns from the two detectors are then cross correlated in time to produce one point on a composite single/multiple scattering function curve. By collecting and analyzing cross correlation measurements that have been taken at a plurality of different spatial/angular positions, the signal representative of single scattering may be differentiated from the signal representative of multiple scattering, and a near optimum detector separation angle for use in taking future measurements may be determined.

18 Claims, 4 Drawing Sheets

OTHER PUBLICATIONS

Phillies, G.D.J.: "Experimental demonstration of multiple-scattering suppression in quasielastic-light-scattering spectroscopy by homodyne coincidence techniques", *Physical Review*, vol. 24, No. 4, Oct. 1981, pp. 1939–1943.

Rička, J.: Dynamic light scattering with single-mode and multimode receivers, *Applied Optics*, vol. 32, No. 15, May 20, 1993, pp. 2860–2875.

Segrè, P.N., W. Van Megen, P.N. Pusey, K. Schätzel and W. Peters: "Two-colour dynamic light scattering", *Journal of Modern Optics*, vol. 42, No. 9, 1995, pp. 1929–1952.

Stieber, F. and W. Richtering: "Fiber-Optic-Dynamic-Light-Scattering and Two-Color-Cross-Correlation Studies of Turbid, Concentrated, Sterically Stabilized Polystyrene Latex", *Langmuir*, vol. 11, No. 12, 1995, pp. 4724–4727.

Weitz, D.A. and D.J. Pine: "Diffusing-wave spectroscopy", *Dynamic Light Scattering*, pp. 652–720.

Wiese H. and D. Horn: "Single-mode fibers in fiber-optic quasielastic light scattering: A study of the dynamics of concentrated latex dispersions", *J. Chem., Phys.*, vol. 94, No. 10, May 15, 1991, pp. 6429–6443.

Berne, B.J., and R. Pecora; *Dynamic Light Scattering*, Wiley, New York, 1976, pp. 1–90.

METHOD AND APPARATUS FOR FIBER OPTIC MULTIPLE SCATTERING SUPPRESSION

RELATED APPLICATIONS

This application claims the benefit of U.S. Provisional Application No. 60/059,619, which application was filed with the Patent and Trademark Office on Sep. 23, 1997, the disclosure of which is incorporated herein by reference.

STATEMENT REGARDING FEDERALLY SPONSORED RESEARCH

This invention was made with Government support under contract Number NAG3-1624 awarded by NASA and Grant Number DMR-9501865 awarded by NSF. The Government has certain rights in this invention.

BACKGROUND OF THE INVENTION

FIELD OF THE INVENTION

This invention relates generally to determining the physical properties of materials through the use of dynamic light scattering, and, more specifically, to a technique for detecting and evaluating singly scattered speckle in concentrated solutions by suppressing the multiply scattered contribution.

BACKGROUND

When light impinges on matter, a portion of that light is scattered or reflected away. The frequency shifts, the angular distribution, the polarization, and the intensity of the scattered light are determined by the size, shape, and molecular interactions of the particles in the scattering material. Thus, from the light-scattering characteristics of a given system it is possible, with the aid of electrodynamics and the theory of time-dependent statistical mechanics, to obtain information about the structure and molecular dynamics of the scattering medium.

Dynamic light scattering exploits the time dependent coherence loss of scattered light to explore the movement of the scatterers. Its applications range from measurements of molecules or particles smaller than the wavelength of the probing light [1] to the much larger structures of, for example, foam [2]. Small scatterers are easily analyzed through the single scattering of photons. Single scattering occurs when each molecule or particle is exposed to essentially the same incident light as occurs in relatively dilute solutions.

Diffusing Wave Spectroscopy [3] and Correlation Transfer Theory [4] make the investigation of more concentrated colloidal samples possible. Both theories, however, presume a knowledge of the single scattering correlation function. This function is often unknown in practical multiple scattering applications, where the incident light may not equally expose all particles or where certain particles may be exposed to light scattered by other particles. Further, even though an equivalent single scattering decay time can be obtained by using the transmitted intensity relative to a known optical thickness reference, where the standard functional form for the single scattering correlation function as an exponential is known, the form of the mean square displacement must still be assumed. It would therefore be very useful to measure the single scattering contribution inside a multiple scattering sample.

Heretofore, two different schemes have been available for extracting some single scattering information from a multiple scattering sample. One such scheme is a fiber semi-backscattering technique that utilizes scattered photons from a small overlap region between an input and a detecting fiber [5]. In this approach, most of the scattering paths within the sample volume involve only single collisions with particles. However, this method does not yield a systematic way of determining the degree of single scattering for different samples. Additionally, in some cases the solution, or the particles present therein, can coat the detecting fiber (because the fiber may need to be inserted into the sample during measurement), thereby corrupting the received signal.

The other approach focuses on multiple scattering elimination by cross correlating the signal of two different incident wave lengths at the same scattered wave vector for each [6, 7] and is based on the multiple scattering elimination methods of Phillies [8, 9, 10]. Two-Color-Cross-Correlation detects only true single scattering. A drawback of this technique is that it requires extensive careful alignment of two input laser beams and two detectors. Additionally, the turbidity of the sample must be small enough to still exhibit significant single scattering. Thus, the technique is limited to small scattering concentrations that can be increased slightly by reducing the sample dimensions.

It is accordingly an object of the present invention to analyze the single scattering of light in turbid media.

It is a related object to provide an efficient means of suppressing the multiple scattering contribution from an illuminated turbid media so that true single scattering data may be obtained and evaluated.

It is another object that the invention be cost effective from an equipment requirement standpoint, utilizing a single laser input beam and readily available component parts.

Before proceeding to a description of the instant invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

Broadly speaking, the instant invention provides a method and apparatus for estimating single scattering functions - particularly in concentrated solutions. The instant method utilizes two light detectors that are spatially and/or angularly separated and which simultaneously record the speckle pattern from a single sample. The recorded patterns from the two detectors are then cross correlated at zero-lag to produce one point on a composite single/multiple scattering function (S/N) curve. By collecting and analyzing cross correlation measurements that have been taken at a plurality of different spatial/angular positions, the signal representative of single scattering may be differentiated from the signal representative of multiple scattering, and a near optimum detector angle for use in taking future measurements may be determined.

By way of general background, when a laser beam is directed into a scattering medium and reflects from a surface a speckle pattern is often observed. This complex pattern results from interference of electromagnetic radiation which originated from a coherent source but which has followed different paths in reflecting or scattering to the detector. At some points, the total field reflecting from the surface will add constructively and be bright, while at other points the total field will add destructively and be dark. If the laser beam is focused to a small region on the reflecting surface, the speckle size typically increases in dimension at the detector. This diffraction effect is analogous to that observed in single slit diffraction, where the diffraction pattern width increases as the slit width decreases. Further, the single scattered light, arising as it does within the laser beam, will tend to originate from a smaller region than the multiple scattered light which tends to be diffused throughout the sample. For this reason, at the detector the single scattered light will have a broad speckle field compared to the multiple scattered speckle.

Turning now to a discussion of various aspects of the instant invention, according to one preferred embodiment there is provided a method, whereby it is possible to identify and separate the contribution of the multiple scattered light from the single scattered light based on the properties of the respective speckles. Since the single scattering speckle (which arises from inside of the incident laser beam) is correlated over a wider angular or spatial range than is the multiple scattering speckle (which might potentially originate from anywhere within the sample), by using two detectors with an appropriately selected spatial (or angular) separation, it is possible to detect the single scattered speckle and attenuate or exclude the multiple scattered speckle contribution. At each angular setting, the light intensities received within the two detectors are cross correlated in time to produce a single numerical value for that detector angle. By collecting cross correlations at a number of different detector angles, a profile is created that can be used to determine the angular ranges over which multiple and single scattering predominate. From the individual cross correlations and the ensemble of angle and cross correlation pairs, it is additionally possible to estimate the optimum (or near optimum) detector angle to use in collecting future observations, as well as a variety of other useful quantities that pertain to the particles of the laser-illuminated sample.

A preferred apparatus for use with the instant invention suppresses multiple light scattering by using two slightly-tilted detectors that are directed toward the same sample volume which has been illuminated by a narrow laser beam. Further, a mechanism is provided whereby the angle between the two detectors may be continuously adjusted so as to give readings at any selected separating angle. The apparatus further preferably utilizes single-mode fiber optic fibers as detectors, single mode fibers being almost ideal for use in detecting dynamic light scattering in dilute suspensions. Additionally, optical fiber GRIN (i.e., graded index) lenses are preferably used on the ends of the monomode fibers to improve the performance of the invention.

As another preferred embodiment of the instant invention, there is provided an apparatus substantially as described above, but wherein a polarizing filter is placed between the sample and the detectors. In the preferred embodiment, the polarizing filter is placed in one of two orientations with respect to the incident laser beam's polarization plane: it is either oriented to have the same polarization (parallel) or oriented to have a perpendicular polarization (perpendicular). Although both polarization components show multiple scattering contributions, only the parallel component contains evidence of the single scattering signal. Thus, the orientation of the polarizer may be used as part of a preferred embodiment to increase the signal-to-noise ratio and eliminate some of the multiple scattering in the received signal.

According to still another preferred embodiment, the collected ensemble of angle/cross correlation pairs can be used with numerical curve fitting routines to provide an estimate of, by way of example, a two-cumulant representation of the time decay of the intensity correlation function and, thus, an estimate of the particle size. When applied to the polarization embodiment of the instant invention, the curve fitting results for the two polarization components support the theory which calls for larger single scattering speckles in the parallel component, and smaller multiple scattering speckles in both the parallel and perpendicular components.

Finally, in another preferred embodiment the methods described previously are extended to much higher concentrations by detecting the scattering from particles close to the sample boundaries. When the instant apparatus detects the particles close to the boundaries of the sample container, there is no limit on the applicable optical thickness except for the exponential decay of intensity. There are always some multiple scattering contributions present that lead to some non-exponentiality. The main decay, though, is surprisingly accurate and can be used to measure the particle sizes of concentrated samples with ease.

A better understanding of the present invention, its several aspects, and its objects and advantages will become apparent to those skilled in the art from the following detailed description, taken in conjunction with the attached drawings, wherein there is shown and described the preferred embodiment of the invention, simply by way of illustration of the best mode contemplated for carrying out the invention.

DETAILED DESCRIPTION OF THE PREFERRED EMBODIMENT

Figure 1:
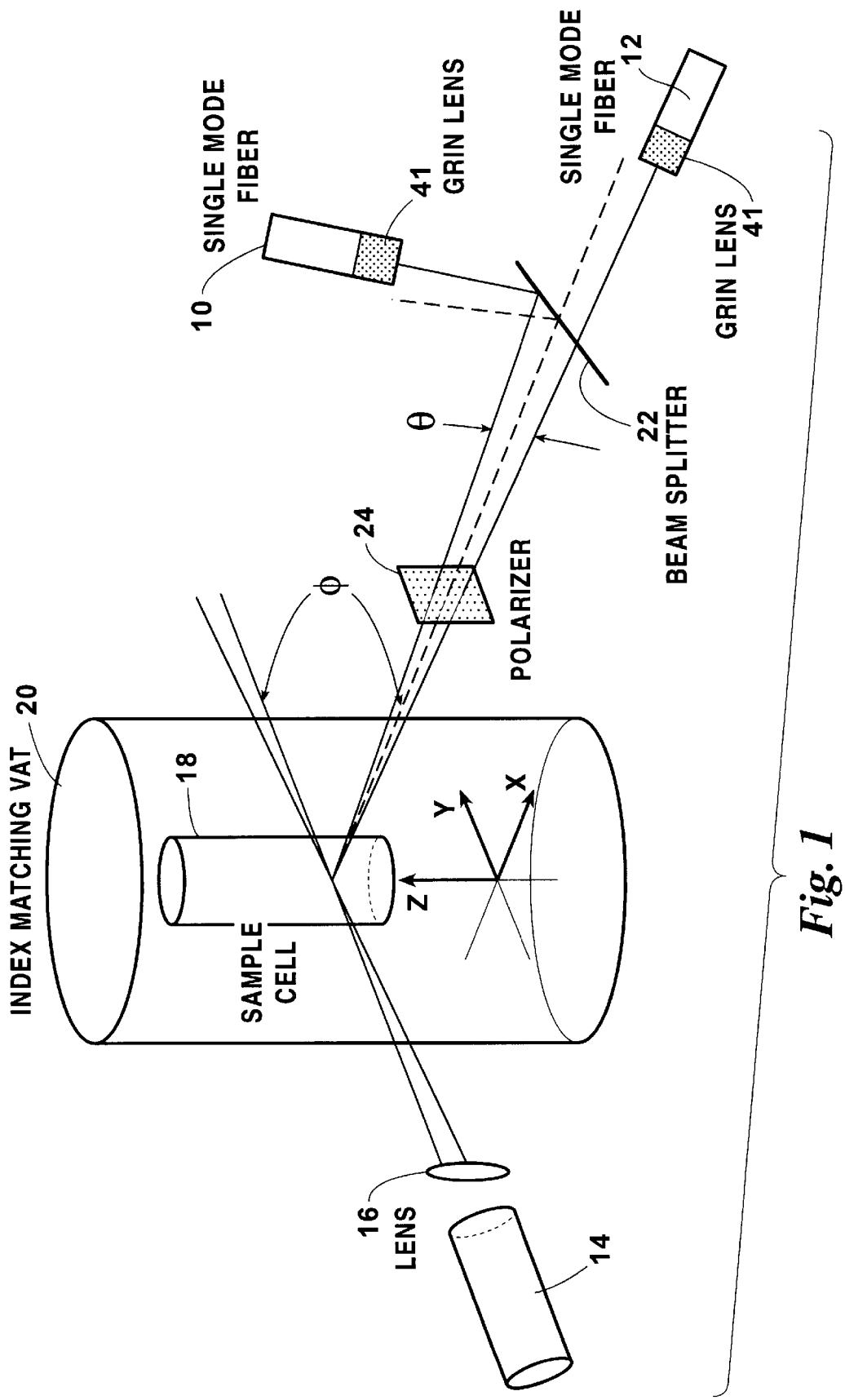
FIG. 1 is a diagram of an experimental setup for the preferred fiber optic multiple scattering suppression technique.

Before explaining the present invention in detail, it is important to understand that the invention is not limited in its application to the details of the construction illustrated and the steps described herein. The invention is capable of other embodiments and of being practiced or carried out in a variety of ways. It is to be understood that the phraseology and terminology employed herein are for the purpose of description and not of limitation.

THEORETICAL BACKGROUND

Broadly speaking, the instant invention utilizes two detectors that are aimed at slightly different angles at a single laser-illuminated sample to record scattered light emanating therefrom. Measurements taken from the detectors over a range of detector angles are used to determine a best angular separation to use so as to observe predominantly the single scattered light component.

By way of explanation, for a Gaussian random process, the intensity correlation function between the two detectors takes the following form [15]:

$$<I(\vec{r}_1,t_1)I(\vec{r}_2,t_2)> = <I(\vec{r}_1,t_1)><I(\vec{r}_2,t_2)>[1+|\gamma(\vec{r}_1,\vec{r}_2,t_1-t_2)|^2]. \quad (1)$$

In this equation, the function $\gamma(\cdot)$ is the second order complex degree of coherence, and $I(\vec{r}, t)$ is the light intensity at the point $\vec{r}$ at time t. The bracket notation (i.e., "<•>") indicates that a time average or expected value is to be taken of the argument (or an ensemble average for a stationary process). In typical dynamic light scattering applications, there is a single detector ($\vec{r}_1 = \vec{r}_2$) and the time dependence of the (auto) correlation function carries the desired information. However, of particular interest for purposes of the instant invention is the signal-to-noise ratio or the complex degree of coherence when $t_1=t_2$, for a similar signal measured by two detectors oriented at slightly different angles. If intensities originating at different regions in the scattering volume are spatially uncorrelated, then the van Cittert-Zernike theorem in the far field limit gives [16]:

$$\gamma(\vec{r}_1, \vec{r}_2, 0) = \frac{\int I(\vec{r}')\exp[-ik(\vec{s}_1 - \vec{s}_2)\cdot \vec{r}']d^3r'}{\int I(\vec{r}')d^3r'}.$$

In the previous equation, $k=2\pi n/\lambda$ is the wave vector of the elastically scattered radiation having wavelength $\lambda$ in the medium with refractive index n. The unit vectors $\vec{s}_1$ and $\vec{s}_2$ point from an origin in the scattering volume to the two detector positions. Note that the previous integration has been extended from a two dimensional surface integral to a three dimensional volume integral to accommodate scattered light coming from a three dimensional volume. The light intensity $I(\vec{r}')$ is determined by the overlap of the incident beam, the multiple scattering within the sample volume, and the field of view of the detectors. A phase factor has been ignored in the above expression because it makes no contribution to $|\gamma(\vec{r}_1,r_2,0)|^2$, the quantity measured in the preferred embodiment of the instant invention.

FIG. 1 shows a preferred two-detector scattering geometry for use with the instant invention, wherein the scattering angle $\phi$ has been selected to be about equal to ninety degrees and the incident beam lies in the xy plane. Note that the geometry illustrated in that figure—including the choice of a particular value for the parameter $\phi$—is just one of many that could be used and it is well within the ability of those skilled in the art to devise other arrangements. The two detectors 10, 12 in FIG. 1 are preferably oriented in the xz-plane and each forms an (extremely) small (e.g., mrad) angle $\theta/2$ with respect to the x-axis. That being said, it is not essential to the operation of the instant invention that the detectors be oriented in any particular plane nor set at any particular scattering angle $\phi$. It is anticipated, though, that generally the detectors and sample detection volume will be aligned in a plane which contains a direction that is perpendicular to the direction of the incident beam. The single scattered speckle is elongated compared to the multiple scattered speckle in these directions. It is required, though, that the two detectors 10 and 12 be aimed toward the sample in such a way that they detect substantially the same portion of the scattered field and that the angle between their respective lines-of-sight be very small.

Further note in FIG. 1 that, strictly speaking, the detectors 10 and 12 are not both aimed directly at the sample, but rather a beam splitter 22 allows detector 10 to be aimed in a direction that is roughly transverse to the direction in which detector 12 is aimed and still detect the scattered field.

The beam splitter 22 was used for purposes of convenience only, and it is not a requirement of the instant invention that the detectors 10 and 12 be so oriented. The net effect, however, is to obtain signals from the detectors that are comparable to those that would have been obtained if the detectors had both been directly aimed at the sample 18. Finally, in the text that follows the detectors will be spoken of as though they are both pointed directly toward the sample 18, but those skilled in the art will understand that mirrors, beam splitters, etc. make it possible to position the detectors 10 and 12 in almost any arbitrary orientation.

The input laser 14 is preferably positioned in the xy-plane at an angle $\phi$ (the "traditional" scattering angle) with respect to the x-axis. For $\phi=90$ degrees, the incident beam is thus parallel to the y-axis, and the x-axis preferably bisects the angle $\phi$, i.e., theta is the angular separation of the unit vectors $\vec{s}_1$ and $\vec{s}_2$, which unit vectors lie in the x-z plane.

Because $\phi$, which is usually about 1 radian, is typically much larger than $\theta$, which is preferably measured in milliradians, the magnitude of the scattering wave vector is well approximated by the standard expression:

$$q=4\pi n \sin(\phi/2)/\lambda,$$

where "n" is the refractive index of the fluid suspension. The field of view of detector 10 is, thus, approximated by the following "gaussian tube":

$$I_1(x,y,z)=\exp(-\alpha(y^2+(z\cos(\theta/2)-x\sin(\theta/2))^2)).$$

Here $1/\sqrt{\alpha}$ is the radius of the 1/e point for the intensity if the field of view is uniformly illuminated. The field of view for detector 12 is similarly approximated by:

$$I_2(x,y,z)=\exp(-\alpha(y^2+(z\cos(\theta/2)+x\sin(\theta/2))^2)).$$

The incident beam intensity is approximated by $$I_{ss}(x,y,z)=B\exp(-\beta(z^2+(x\sin(\phi)+y\cos(\phi))^2)),$$

where the maximum intensity on-axis is given by the parameter "B". The multiple scattered intensity is assumed to be uniformly distributed with magnitude "A" and it is further assumed to be incoherent with respect to the incident beam at the same location. This simply means that the incident and multiple scattered intensities are added together, rather than adding their field amplitudes and squaring the result. Finally, the finite size of the sample 18 is represented by a Gaussian cutoff function:

$$I_{gc}(x,y,z)=\exp(-2\delta(x^2+y^2+z^2)).$$

Combining these factors together as they occur in the preferred measurement geometry yields:

$$\gamma(\vec{r}_1, \vec{r}_2, 0) =$$

$$\frac{\int \exp(-i2kz\sin(\theta/2))I_1(x,y,z)I_2(x,y,z)I_{gc}(x,y,z)(A+I_{ss}(x,y,z))d^3r}{\int I_1(x,y,z)I_2(x,y,z)I_{gc}(x,y,z)(A+I_{ss}(x,y,z))d^3r}$$

Assuming a small focused laser beam and an intermediate detection width and a large sample volume, then the parameters $\beta$, $\alpha$, and $\delta$ will be assumed to have the following relationship: $\beta>>\alpha>>\delta$. Further, since the angle between the detectors, $\theta$, is extremely small, the standard substitutions $\sin(\theta)\approx\theta$ and $\cos(\theta)\approx 1$ may be used. It is also fair to assume that $\phi>>\theta$ which leads, in turn, to the inequality:

$\beta$ (sin$\phi$)$^2$>>$\delta$. Given these simplifications and assumptions, a simplified expression for $\gamma(\theta)$ may be developed:

$$\gamma(\theta) = \frac{A\frac{\exp(-k^2\theta^2/(8\alpha))}{(\alpha^2(\alpha\theta^2/4+\delta))^{1/2}} + 2B\frac{\exp(-k^2\theta^2/(4\beta\alpha))}{\beta\sqrt{\alpha}\sin\phi}}{\frac{A}{\alpha\sqrt{\delta}}+\frac{2B}{\beta\sqrt{\alpha}\sin\phi}}$$

The square of this function gives the signal to noise ratio in equation 1 when $t_1=t_2$. The normalized intensity correlation function $G^{(2)}(\tau)$ is then related to the normalized field correlation function $G^{(1)}(\tau)$ by $$G^{(2)}(\tau)=1+\gamma(\theta)^2(G^{(1)}(\tau))^2.$$

Note that various assumptions and approximations have been made in the derivation of the foregoing that were designed to expedite the evaluation of some of the integral formulas. However, those skilled in the art know that these substitutions were only representative of the many others that could have been made and are not critical to the practice of the instant invention. Thus, the various simplifying assumptions listed herein have been made for purposes of computational convenience only rather than out of any intent to limit the instant method to any one particular method of obtaining, solving, and evaluating the previous equations.

PREFERRED APPARATUS

In a preferred apparatus embodiment of the instant invention—and as is shown generally in FIG. 1—a Helium Neon laser 14 ($\lambda$=632.8 nm) is focused with a lens 16 of focal length 5 cm into a cylindrical sample cell 18 1 cm in diameter. The sample cell 18 is preferably immersed in a larger water bath cylinder 20 (6.5 cm diameter) to reduce parasitic scattering effects. A beam waist radius of approximately 30 $\mu$m is calculated based on the beam size (0.68 mm radius for the intensity 1/e points) and Gaussian optics. This calculation ignores the influence of the index of refraction change of the water bath by using the focal length of 5 cm in air. The true beam diameter should be larger due to refraction effects. In practice, the instant inventor has found that a beam radius of 50 $\mu$m corresponding to $\beta$=4·10$^8$/m$^2$ fits the experimental results best.

Figure 2:
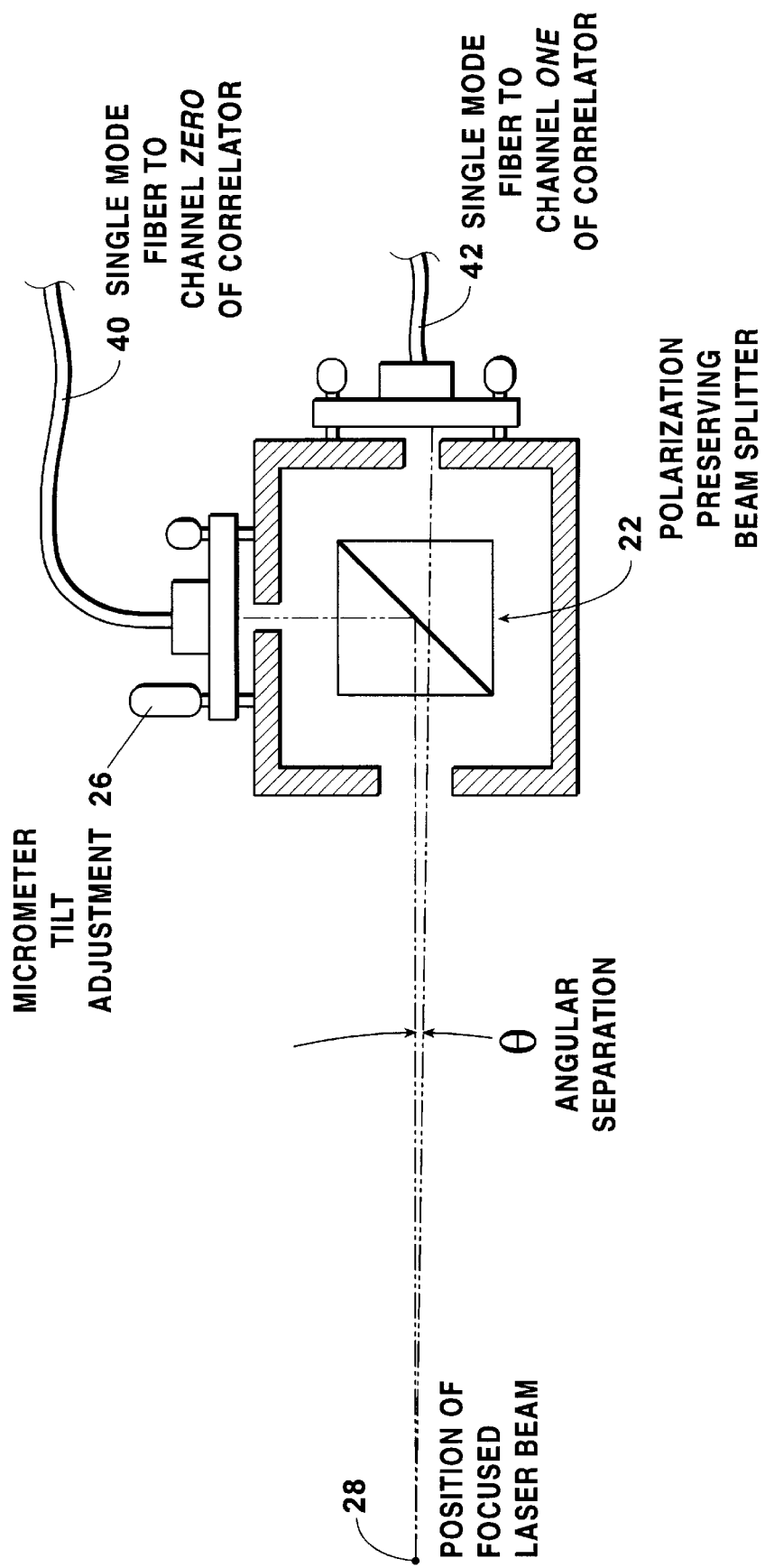
FIG. 2 is a diagram of the preferred detecting assembly.

As in conventional dynamic light scattering, the sample 18 is illuminated by a tightly focused laser beam, such as is indicated at point 28 in FIG. 2, the scattering therefrom being captured by the two detectors 10 and 12 which are oriented at detector angle $\theta$ with respect to each other. Note that, when the detector angle is zero, normal dynamic light scattering results and the recorded signal will typically be contaminated by a multiple scattered component. However, as the angular separation between the detectors increases the multiple scattering component of the signal decreases and ultimately only a single scattering signal remains.

Two single mode fibers 40, 42 are preferably used as detectors and are aligned through a beam splitting cube 22 to the focal spot of the laser inside the sample, beam splitter 22 preferably being a polarization preserving beam splitter. A rough alignment is accomplished by reversing the detection light path with a second auxiliary HeNe laser to arrive at an overlap of the incident and "detecting" beams. By way of example, in the preferred arrangement a HeNe beam directed through the fibers shows a divergence of 1.5 mrad.

To determine the minimum detector angle necessary to record only the single scattering field, a scan over a range of detector angles $\theta$ is performed. In the preferred embodiment, the scattering angle, $\phi$, is chosen to be 90° and the two detectors 10, 12 are arranged so as to deviate only a few mrads from $\phi$ and are preferably positioned above and below the usual scattering plane. That being said, many other choices of scattering angle could have been used instead and that possibility has been specifically contemplated by the instant inventor.

As is shown with more particularity in FIG. 2, the detector angle is preferably varied with a micrometer 26 that tilts the plane of one detector 10 with respect to the other 12. Although adjustment with a micrometer is the presently preferred method of changing the tilt angle and, hence, the angle between the two detectors 10 and 12, there are many other ways to accomplish this same task. By way of example, other ways that the detector angle might be adjusted include moving the two detectors laterally apart, or closer to (farther away from) the source, utilizing a curved beam splitter, etc. Thus, as used hereinafter, the term "micrometer" will be broadly construed to refer any mechanism that can be used to adjust the orientation of at least one of the detectors so as to change the detector angle $\theta$ in very small (e.g., mrad) increments.

According to another embodiment of the instant invention, an apparatus substantially as described above is used, but each detector 10 and 12 is further provided with a GRIN lens 41 that intercepts the speckle data before it enters the single mode fibers 40 and 42. As is well known to those skilled in the art, a GRIN (i.e., graded index) lens is a lens that has a refractive index that gradually changes from a relatively high value at its core to a lower value at its periphery. Thus, the refractive index decreases with the distance away from its core axis as a function of radius. In a GRIN lens, a process of continuous refraction bends rays of light such that Snell's law is obeyed on a microscopic scale. Light ray containment now occurs by a process of continuous refraction. Among the many advantages of GRIN lenses are that they result in better detection efficiency. One GRIN lens that would be suitable for use with the instant invention is a model designed for 633 nm and sold by OZ-Optics, Canada. In the preferred embodiment, each GRIN lens 41 will be about 2 mm in length and made as an integral part of both ends of the single mode fibers 40 and 42.

If a GRIN lens is used, the detector field of view approximated as a cylinder has a diameter of 1.1 mm (fiber divergence angle times fiber distance) and corresponds to $\alpha$=3.3·10$^6$/m$^2$. A detector field cylinder diameter of 0.9 mm was found to improve the fit. By assuming that the multiple scattering sample volume is a sphere of ≈1 cm, the value of the parameter $\delta$ can be taken to be 4·10$^4$/m$^2$. The cross correlation of the detector signals is preferably obtained with an ALV1-5000/E correlator (not shown). That being said, it is also possible to separately digitize the light signal received by each detector 10 and 12 and store those numerical values for later computation. In that case, additional manipulations of the two signals would be possible including, by way of example, frequency domain analyses, time domain analyses, analyses of mathematical functions of the digitized detector signals, statistical analysis, cross correlations at other than zero lag, etc., any of which might potentially prove to be useful in a given situation.

The tilt angle discussed previously that is created by the adjustments to the micrometer position 26 is preferably calibrated by reversing a laser beam through the single mode fiber 40 and noting the angular change on a screen placed some distance away from the apparatus. After the application of a given tilt, the detector typically has to be translated slightly to align it with the incident beam and to maximize the detected intercept. It has been the inventor's experience that this translation can be extremely sensitive to even a slight touch of the controls. This sensitivity is believed to be a principal reason for the scatter observed in the data points discussed hereinafter.

According to still another aspect of the instant invention, there is provided an to apparatus substantially as described above, but wherein a polarizing filter is positioned to intercept the speckle data before that data reaches the detector. As is well known to those skilled in the art, a polarizing filter attenuates light passing therethrough that is not oscillating in a preferred plane. By placing a properly oriented polarizer between the sample and the detectors, some of the multiple scattering will be eliminated and the signal-to-noise ratio will be thereby increased.

Finally, according to another useful embodiment of the instant invention, the apparatus was further arranged so as to be suitable for to measuring particle sizes in a polystyrene sample of 2% volume fraction. The arrangement of the detectors 10 and 12 is the same as that shown in FIG. 1, but the sample 18 and water bath 20 are preferably replaced by a sample in a rectangular cell. The cell can be placed in an angular range of approximately 15–60° with respect to the incident laser direction (this angle is important for the scattering angle determination), and the laser is focused near the surface of the sample 18. The detectors 10 and 12 are aligned to measure at the focal point and are preferably tilted about 1 mrad with respect to each other. This skin layer scattering technique works very well for the highly concentrated volumes. It maximizes the visible single scattering while the tilted fibers suppress the attendant multiple scattering.

ANALYSIS

According to one preferred mode of data analysis, the intensity cross correlation function obtained from the two detectors 10 and 12 at a particular d etector angle θ' is fitted with a two-cumulant expansion of the form $$G^{(2)}(\tau)=1+\gamma^2(\theta')\exp(-2u\tau+2v\tau^2)$$

using the signal-to-background fitting factor $\gamma^2(\theta')$ defined previously, where $\tau=t_1-t_2$ is the delay time, typically measured in microseconds, and where $G^{(2)}(\tau)$ is the normalized intensity cross correlation function between the two detector signals at the fixed detector angle θ. Although this function might be estimated in many ways, in the preferred embodiment a non-linear least squares routine is used to produce estimates of the parameters u and v. Provided that the detector angle has been chosen in the range wherein single scattering predominates and wherein the multiply scattered signal is attenuated, the fitted value of the first cumulant u may then be used to estimate the particle radius r in the scattering medium through its connection with the Einstein diffusion coefficient D and the wave vector q:

$$u = Dq^2 = \frac{k_B T}{6\pi\eta r}\left(\frac{4\pi n}{\lambda}\sin\left(\frac{\phi}{2}\right)\right)^2$$

Theoretically speaking, the previous equation requires that the particles whose size is to be estimated be freely diffusing and non-interacting as those terms are known in the art, e.g., particles in suspension. Of course, where there is a distribution of particle sizes—rather than a perfectly uniform sample—the instant method will return the z-average size of the particle distribution Thus, in the text that follows when a sample particle size is determined, it will be understood to be some sort of average or composite measure such as the z-average size if the sample contains particles of different sizes.

In the previous equation, the parameter $k_B$ denotes the Boltzmann constant, T is the absolute temperature, n is the refractive index of the suspension, η the viscosity of the sample and λ the laser wavelength. Additionally, the normalized second cumulant $v/u^2$ is an indicator of the "quality" of the fit since, for absolutely monodisperse spherical particles in single scattering, the normalized second cumulant should vanish. The normalized second cumulant is also an indicator of the variance of particle sizes in the sample, i.e., for a sample containing particles with a distribution of sizes, this parameter can be an indicator of the polydispersity (i.e., the relative width of the size distribution). In the examples that are discussed below, normalized second cumulant values less then or equal to about 0.05 in the dilute single scattering limit are expected.

EXAMPLES

In the specific examples that are presented hereinafter, the sample consisted of polystyrene spheres of diameter 0.107 μm manufactured by Duke Scientific (5.6% CV, Lot 16203) and diluted with water to 0.15 and 0.25% volume fraction. It should be noted that these examples are offered for purposes of illustration only and are not intended to limit the scope of application of the instant invention.

Figure 3:
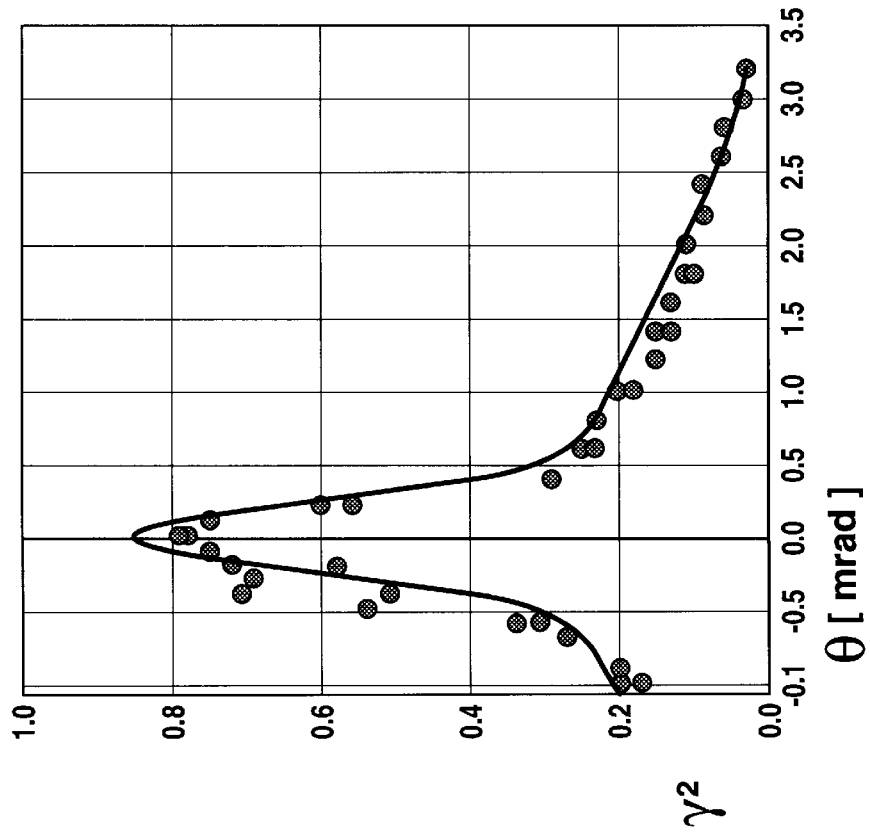
FIG. 3 is a representative plot of intercept versus angular tilt for the cross correlation of a multiple scattering sample.

FIG. 3 contains a plot of the signal-to-background for a range of different detector angles θ for a lower volume fraction sample. The solid line that is drawn over the experimental measurement points is the expected behavior of a sample with an assumed ratio (A:B) of multiple to single scattering of 1:600. (PST 0.107 μm, Φ=0.0015). Great care was taken in this particular experiment to measure $\gamma^2$ near θ=0. Note that for larger θ the measured value of $\gamma^2$ is more stable and reproducible and that the highest possible single scattering intensity auto-correlation function $\gamma^2$ occurs at about 0.85. Therefore the fitting function (which is given by the square of the function for γ(θ) given previously) was multiplied by this factor. Additionally, note that measurements corresponding to negative values of θ were also taken and that, as expected, those measurements proved to by symmetric about an angle of zero.

FIG. 3 clearly indicates the presence of different speckle sizes: the central narrow peak corresponds to the multiple scattering speckle and the broader peak underneath is the single scattering speckle originating from the smaller single scattering volume.

Figure 4:
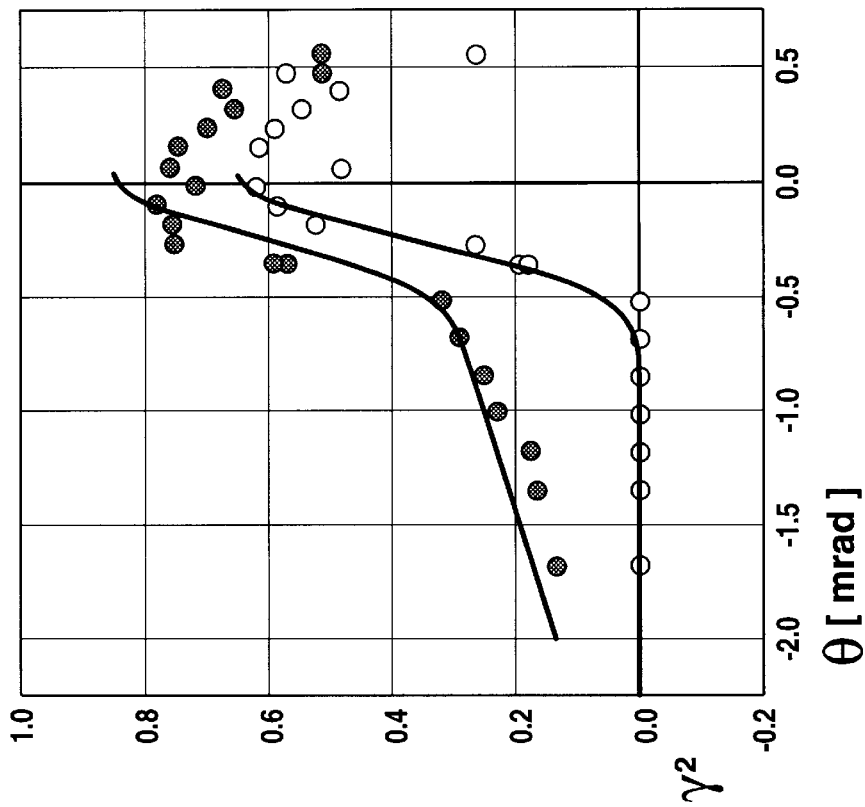
FIG. 4 is a representative plot of intercept versus angular tilt for the two polarizations of a multiple scattering sample.

The previous tilt angle scan was repeated for an even more concentrated 0.107 μm polystyrene sample, the results of which are presented in FIG. 4. There are two data sets in this figure, each of which was collected after passing the incoming speckle data through a polarizer: one data set was obtained with a polarizer that selected the same polarization (parallel) as the incident laser beam's polarization plane, while the other set oriented to pass only the perpendicular component. The filled circles in FIG. 4 result from a two cumulant fit to the time dependent cross correlation function of the parallel polarization component, whereas the open circles represent the perpendicular polarization data. The solid lines on that plot have been calculated with an assumed ratio (A:B) of multiple to single scattering of 1:700 for the parallel and 1:0 for the perpendicular component. (PST 0.107 μm, Φ=0.0025).

In FIG. 4, the parallel component shows a high intercept in the multiple scattering center region and then drops significantly to a shoulder region just as did the data in FIG. 3. The intercept of the perpendicular polarization effectively vanishes for angles below-about –0.5 mrad, because the single scattering signal is severely attenuated by the polarizing filter. The lines in this figure are calculated from the normalized intensity correlation function ($G^{(2)}(\tau)$, previously), but with an additional multiplying amplitude factor of 0.85 for the parallel and 0.65 for the crossed polarization signals as determined from the autocorrelation results discussed previously. A ratio of multiple to single scattering of 1:700 for the parallel and 1:0 for the perpendicular component is assumed: all other parameters remained unchanged. The single scattering contribution for the previous, more dilute, sample was smaller because the polarization of the incident laser was misaligned with respect to the scattering plane normal. Here, the incident polarization vector is perpendicular to the scattering plane.

Figure 5:
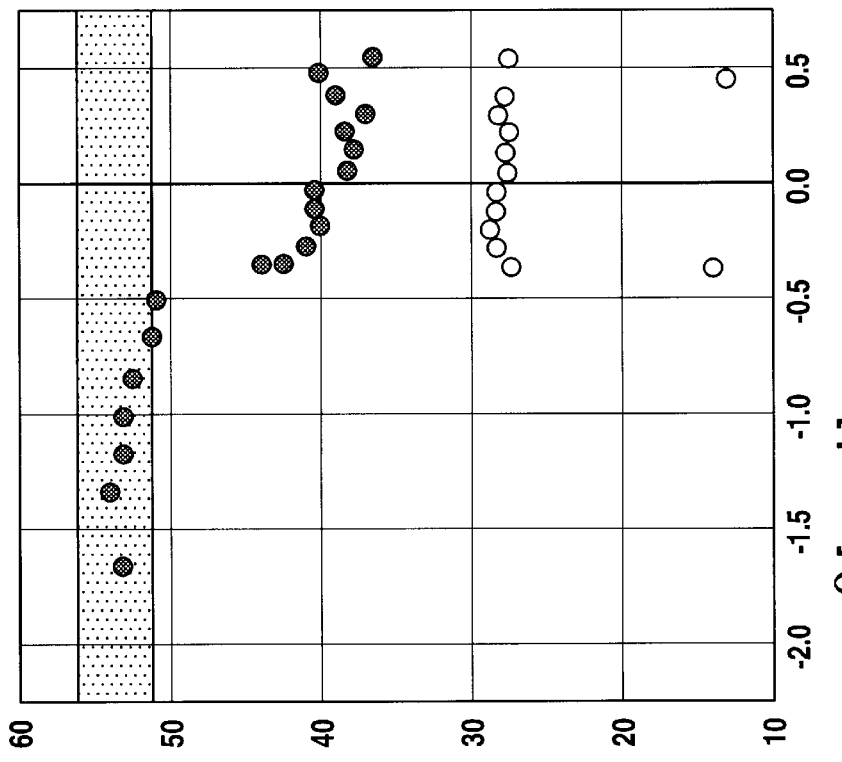
FIG. 5 is a representative plot of particle size (nm) versus angular tilt for the two polarizations of a non-single scattering sample.

FIG. 5 contains a comparison of the results obtained during a test of a second 0.107 μm diameter polystyrene sample for the two polarization components. The filled circles are the radii obtained from a fit to the cross correlation function of the parallel polarization component, and the open circles are fits to the perpendicular polarization data. The cross hatched area is the expected size based on a single scattering analysis. (PST 0.107 μm, Φ=0.0025). In FIG. 5, note that when the calculated fits are based on the perpendicular polarization component, the particle radii determined from the cumulant fit are substantially smaller than the actual value of 53.5 nm. This is primarily because, in this polarization orientation, only multiple scattering is observed. On the other hand, calculations based on the parallel polarization component gave very good particle size estimates where the angular separation was greater than about 0.5 mrad in magnitude. More particularly, at about 1 mrad the influence of single scattering predominates and the calculations produce an acceptable size estimate. For detector angle magnitudes less than 0.5 mrad, the multiple scattering component is not sufficiently attenuated and the particle size estimates are correspondingly affected. In general, as the angular tilt is increased the cross correlation loses most multiple scattering contributions and produces increasingly better estimates.

FIGS. 3–5 confirm that the multiple scattering speckle decreases faster with detector separation angle then the single scattering speckle. It is always present regardless of choice of polarization orientation or the presence or absence of the single scattering speckle. The single scattering speckle, however, disappears when the detected polarization is perpendicular to the incident polarization (a forbidden "transition" for single scattering). The perpendicular correlation function decays faster than the parallel one because it contains relatively more multiple scattering. As the detector angle increases the correlation function begins to disappear. There is no detectable signal in the single scattering shoulder.

Figure 6:
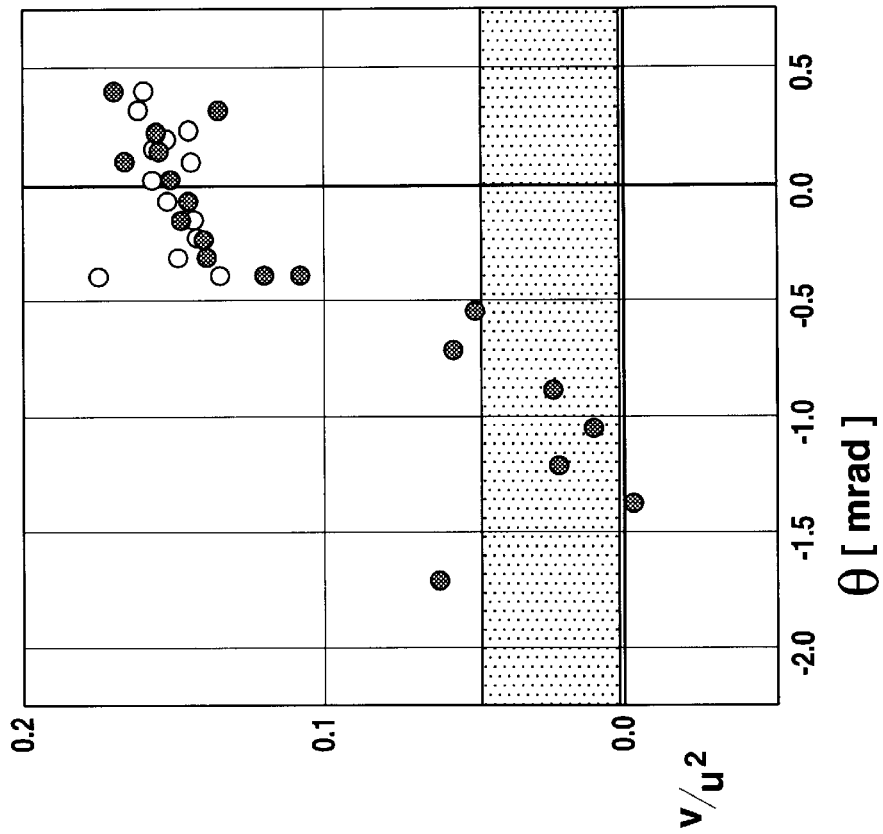
FIG. 6 is a representative plot of normalized second cumulant versus angular tilt for two polarizations of a non-single scattering sample.

As was discussed previously, the value of the normalized second cumulant is a measure of the exponentiality of the correlation function. A small second cumulant (for monodisperse particles) is a good indication of a single scattering correlation function. If multiple scattering adds a faster decaying contribution to the correlation function, the functional form will change. This non-exponentiality will surface in the form of a relatively large value of the normalized second cumulant. This contention is confirmed with the data in FIG. 6. As before, the filled circles are the fits to the cross correlation function of the parallel polarization component, and the open circles represent the perpendicular polarization data. The cross hatched area represents the single scattering expectation for this sample. (PST 0.107 μm, Φ=0.0025). In the multiple scattering region of the detector angle, the second cumulant is significantly above 10%. It drops to about 0.05 in the single scattering regime.

CONCLUSIONS

The present invention is thus an improvement over the well known ALV Dual Color light scattering apparatus in that it is significantly less expensive to set up and to maintain. Though the apparatus described above was originally set up to examine the speckle structure as described by W. Meyer et al. in reference 13 of the following bibliography, its capabilities are enhanced relative prior techniques. Meyer et al. do not use GRIN lens fibers but utilize a sample temperature control bath and/or index matching vat as a lens for the fibers. In highly multiple scattering samples, where beam attenuation is significant, it will be best to detect the light scattering from a flat cell surface at the entrance point of the beam. This maximizes the single scattered signal and allows scattering angle studies to be made. Under these practical situations, the GRIN lens system is superior. Furthermore, the GRIN lens system may be adjusted to optimize the single scattered signal by finding the angle θ which is just outside the multiple scattering signal. This is not possible in the system of Meyer it al.

The multiple scattering suppression techniques described herein will be useful in any dynamic light scattering experiment where multiple scattering is a problem and single scattering signals are desired, e.g., particle sizing in optically dense colloidal systems including paints, oil, gels, flocks, porous media, smoke, biomolecules; microsensors in monitoring fluid quality and process control.

While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

BIBLIOGRAPHY

The following papers and other publications are incorporated herein by reference:

[1] B. J. Bere, and R. Pecora; *Dynamic Light Scattering*, Wiley, New York (1976).

[2] D. H. Duian, D. A. Weitz, and D. J. Pine; "Multiple Light-Scattering Probes of Foam Structure and Dynamics" *Science* 252, 686–688 (1991).

[3] D. A. Weitz, and D. J. Pine; "Diffusing-Wave Spectroscopy" in *Dynamic Light Scattering: the Method and some Applications*, ed. Wyn Brown, Oxford University Press, New York, 652–720 (1993).

[4] R. L. Dougherty, B. J. Ackerson, N. M. Reguigui, F. Dorri-Nowkoorani, and U. Nobbmann; "Correlation Transfer: Development and Application" *J. Quant. Spectrosc. Radiat. Transfer* 52, 713–727 (1994).

[5] H. Wiese, and D. J. Horn; "Single-Mode Fibers in Fiber-Optic Quasielastic Light Scattering: A Study of the Dynamics of Concentrated Latex Suspensions" *J. Chem. Phys.* 94, 6429–6443 (1991).

[6] P. N. Segre, W. Van Megen, P. N. Pusey, K. Schatzel, and W. Peters; "Two-Color Dynamic Light-Scattering" *J. Mod. Opt.* 42, 1929–1952 (1995).

[7] F. Stieber, and W. Richtering; "Fiber-Optic-Dynamic-Light-Scattering and Two-Color-Cross-Correlation Studies of Turbid, Concentrated, Sterically Stabilized Polystyrene Latex" *Langmuir* 11, 4724–4727 (1995).

[8] G. D. J. Phillies; "Suppression of Multiple-Scattering Effects in Quasielastic-Light-Scattering Spectroscopy by Homodyne Cross-Correlation Techniques", *J. Chem. Phys.* 74, 260–262 (1981).

[9] G. D. J. Phillies; "Experimental Demonstration of Multiple-Scattering Suppression in Quasielastic-Light-Scattering Spectroscopy by Homodyne Coincidence Techniques", *Phys. Rev. A* 24, 1939–1943 (1981).

[10] J. K. G. Dhont, C. G. de Kruif; "Scattered light intensity cross correlation. I. Theory", *J. Chem. Phys.* 79, 1658–1663 (1983).

[11] R. G. W. Brown; "Dynamic Light Scattering using Mono-Mode Optical Fibers" *Appl. Opt.* 26, 4846–4851 (1987).

[12] J. Ricka; "Dynamic Light Scattering with Single-Mode and Multimode Receivers" *Appl. Opt.* 32, 2860–2875 (1993).

[13] W. V. Meyer, D. S. Cannell, A. E. Smart, T. W. Taylor, and P. Tin; "Suppression of Multiple Scattering using a Single Beam Cross-Correlation Method" in *Light Scattering and Photon Correlation Spectroscopy ed.* E. R. Pike and J. B. Abiss, NATO ASI Series, Kluwer Publishers, Dordrecht (1997).

[14] J. A. Lock; "The Role of Multiple Scattering in Cross-Correlated Light Scattering Employing a Single Laser Beam", submitted to *Appl. Opt.* (1997).

[15] L. Mandel, and E. Wolf; *Optical Coherence and Quantum Optics*, Cambridge University Press, New York (1994), p. 428.

[16] L. Mandel, and E. Wolf; *Optical Coherence and Quantum Optics*, Cambridge University Press, New York (1994), p. 188ff.

[17] W. V. Meyer, D. S. Cannell, A. E. Smart, T. W. Taylor, and P. Tin; "Multiple-scattering suppression by cross correlation", *Applied Optics*, 36, 7751–7558 (1997).

What is claimed is:

1. A method of determining a particle size using dynamic light scattering, wherein is provided a sample containing a plurality of particles, comprising the steps of:
    (a) directing a laser light beam at the sample, thereby creating a speckle field containing at least a multiply scattered signal and a singly scattered signal;
    (b) orienting a first detector so as to detect a predetermined portion of the speckle field;
    (c) orienting a second detector so as to detect substantially the same predetermined portion of the speckle field, said second detector being aligned at a predetermined small angle with respect to said first detector;
    (d) simultaneously detecting the predetermined portion of the speckle field within said first detector and said second detector, thereby creating a first detector signal and a corresponding second detector signal;
    (e) performing steps (b) to (d) at a plurality of different predetermined small angles, thereby producing a plurality of first detector signals and a corresponding plurality of second detector signals; and,
    (f) determining an estimate of the particle size using said plurality of first detector signals and said corresponding plurality of second detector signals.

2. A method according to claim 1, wherein step (d) includes the step of:
    (d1) calculating a cross correlation between said first detector signal and said second detector signal, thereby forming an intensity cross correlation value, and, wherein step (f) includes the step of:
    (f1) determining an estimate of the particle size using any intensity cross correlation values so calculated.

3. A method according to claim 1, wherein step (f) includes the steps of
    (f1) selecting a particular first detector signal from among said plurality of first detector signals,
    (f2) selecting a corresponding second detector signal from among said corresponding plurality of second detector signals,
    (f3) cross correlating said selected first detector signal and said selected second detector signal, thereby producing an intensity cross correlation value,
    (f4) performing steps (f1) to (f3) for a plurality of different particular first detector signals and corresponding second detector signals, thereby producing a plurality of intensity cross correlation values, and,
    (f5) determining an estimate of the particle size using said plurality of intensity cross correlation values.

4. A method of determining a particle size using dynamic light scattering according to claim 3, wherein step (f5) includes the steps of:
    (1) determining from said plurality of intensity cross correlation values a particular detector angle, whereat the multiply scattered signal is attenuated with respect to the singly scattered signal,
    (2) orienting said first detector so as to detect a portion of the speckle field,
    (3) orienting said second detector so as to detect substantially a same portion of the speckle field, said second detector being aligned at said particular detector angle with respect to said first detector,
    (4) simultaneously detecting the speckle field within said first detector and said second detector, thereby creating a first detector signal and a second detector signal,
    (5) cross correlating said first detector signal and said second detector signal, thereby producing a cross correlation function, and,
    (6) determining an estimate of the particles size using at least a portion of said cross correlation function.

5. A method of determining a particle size using dynamic light scattering according to claim 1, wherein step (f) includes the steps of:
    (f1) determining from said plurality of first detector signals and said corresponding plurality of second detector signals a particular detector angle, whereat the multiply scattered signal is attenuated with respect to the singly scattered signal,
    (f2) orienting said first detector so as to detect a portion of the speckle field,
    (f3) orienting said second detector so as to detect substantially a same portion of the speckle field, said second detector being aligned at said particular detector angle with respect to said first detector,
    (f4) simultaneously detecting the speckle field within said first detector and said second detector, thereby creating a first detector signal and a second detector signal,
    (f5) cross correlating said first detector signal and said second detector signal, thereby producing a cross correlation function, and,
    (f6) determining an estimate of the particles size using at least said cross correlation function.

6. A method of attenuating multiple scattering in dynamic light scattering measurements, wherein is provided a sample containing particles, comprising the steps of:

(a) directing a laser light beam at the sample, thereby creating a speckle field having a multiple scattering component and a single scattering component;

(b) orienting a first detector to detect a predetermined portion of the speckle field;

(c) orienting a second detector to detect substantially a same predetermined portion of the speckle field, said second detector being aligned at a predetermined small angle with respect to said first detector;

(d) simultaneously detecting the predetermined portion of the speckle field within said first detector and said second detector, thereby creating a first detector signal and a second detector signal;

(e) cross correlating said first detector signal and said second detector signal, thereby producing an intensity cross correlation value;

(f) performing steps (b) to (e) at a plurality of different predetermined small angles, thereby producing a plurality of intensity cross correlation values; and, (g) determining from said plurality of intensity cross correlation values an optimizing detector angle between said first detector and second detector, whereat said multiple scattering component is attenuated and whereat said single scattering component predominates.

7. A method of attenuating multiple scattering in dynamic light scattering measurements according to claim 6, comprising the further steps of:

(h) orienting said first detector to detect a particular portion of the speckle field;

(i) orienting said second detector to detect substantially a same particular portion of the speckle field, said second detector being aligned at said optimizing detector angle with respect to said first detector; and, (j) simultaneously detecting the particular portion of the speckle field within said first detector and said second detector, thereby creating a first optimizing detector signal and a second optimizing detector signal at said optimizing detector angle.

8. A method of attenuating multiple scattering in dynamic light scattering measurements according to claim 7, comprising the further steps of:

(k) determining an estimate of a size of said plurality of particles from said first optimizing detector signal and said second optimizing detector signal.

9. A method of attenuating multiple scattering in dynamic light scattering measurements according to claim 8, wherein said particles are contained in a fluid suspension, wherein step (k) includes the steps of:

(k1) cross correlating said first optimizing detector signal and said second optimizing detector signal, thereby producing an optimizing intensity cross correlation function, (k2) solving the following equation containing parameters u and v for at least the parameter u, $$G^{(2)}(\tau)=1+\gamma^2(\theta')\exp(-2u\tau+2v\tau^2)$$

where, $\gamma^2(\theta')$ is a signal-to-background fitting factor at said optimizing detector angle, where $\tau$ is a delay time, where $G^{(2)}(\tau)$ is said optimizing intensity cross correlation function, and where $\theta'$ is said optimizing detector angle, and, (k3) solving the following equation for the parameter r, $$u = \frac{k_B T}{6\pi\eta r}\left(\frac{4\pi n}{\lambda}\sin\left(\frac{\phi}{2}\right)\right)^2$$

where r is an estimate of said size of said particles, where $k_B$ is Boltzmann's constant, where T is an absolute temperature, where n is a refractive index of said fluid suspension, where $\eta$ is a viscosity of the sample, where $\lambda$ is a laser wavelength of said laser beam, and where $\phi$ is said optimizing detector angle.

10. A method of determining particle size in a sample, wherein is provided said optimizing detector angle of claim 6 step (g), and wherein is provided a new sample, comprising:

(a) directing a laser light beam at the new sample, thereby creating a new speckle field having a new multiple scattering component and a new single scattering component;

(b) orienting a first detector to detect a predetermined portion of the new speckle field;

(c) orienting a second detector to detect substantially a same predetermined portion of the new speckle field, said second detector being aligned at approximately said optimized detector angle with respect to said first detector;

(d) simultaneously detecting the predetermined portion of the new speckle field within said first detector and said second detector, thereby creating a first detector signal and a second detector signal;

(e) cross correlating said first detector signal and said second detector signal, thereby producing a new intensity cross correlation value;

(f) determining a particle size of the new sample using at least said new intensity cross correlation value.

11. A method of attenuating multiple scattering in dynamic light scattering measurements, wherein is provided a sample containing particles, comprising the steps of:

(a) directing a laser light beam at the sample, thereby creating a speckle field having a multiple scattering component and a single scattering component;

(b) orienting a first detector to detect a predetermined portion of the speckle field;

(c) orienting a second detector to detect substantially a same predetermined portion of the speckle field, said second detector being aligned at a predetermined small angle with respect to said first detector;

(d) simultaneously detecting the predetermined portion of the speckle field within said first detector and said second detector, thereby creating a first detector signal and a corresponding second detector signal;

(e) performing steps (b) to (d) at a plurality of different predetermined small angles, thereby producing a plurality of first detector signals and a corresponding plurality of second detector signals; and, (h) determining from said plurality first detector signals and said corresponding plurality of second detector signals an optimizing detector angle between said first detector and said second detector, whereat said multiple scattering component is attenuated and whereat said single scattering component predominates.

12. An apparatus for suppressing multiple scattering, wherein is provided a sample containing particles, comprising:

(a) a lasing apparatus, said lasing apparatus for producing a laser beam directed at the sample, thereby creating a speckle field signal when so directed;

(b) a first detector positionable to detect at least a portion of the speckle field so created, said first detector generating a first electronic signal representative of any speckle field so detected;

(c) a second detector positionable at a predetermined small angle with respect to said first detector and detecting substantially a same said at least a portion of the speckle field so created, said second detector generating a second electronic signal representative of any speckle field so detected; and, (d) a mechanism for varying said predetermined angle between said first detector and said second detector in approximately mrad increments.

13. An apparatus according to claim 12, wherein said mechanism for varying said predetermined angle between said first detector and said second detector is a micrometer.

14. An apparatus according to claim 12, further comprising:

(e) a beam splitter positionable between the sample and said first and second detectors, said first and second detectors detecting the speckle field through said beam splitter.

15. An apparatus according to claim 12, further comprising:

(e) a polarizing lens between the sample and said first and second detectors, said first and second detectors detecting the speckle field through said polarizing lens.

16. An apparatus according to claim 12, further comprising:

(e) a correlator, said correlator being in electronic communication with said first detector and with said second detector, and said correlator cross correlating said first electronic signal with said second electronic signal, thereby producing at least a cross correlated intensity value.

17. An apparatus according to claim 12 wherein said first detector is a first single-mode optical fiber, said first single-mode optical fiber having a forward terminus positionable to detect at least a portion of the speckle field, and wherein said second detector is a second single-mode optical fiber, said second single-mode optical fiber being positionable to detect substantially a same said at least a portion of the speckle field.

18. An apparatus according to claim 17 wherein said forward terminus of said first single-mode optical fiber further includes a GRIN lens and wherein said forward terminus of said second single-mode optical fiber further includes a GRIN lens.

* * * * *